(12) United States Patent
Miller et al.

(10) Patent No.: US 10,806,325 B2
(45) Date of Patent: Oct. 20, 2020

(54) METHODS AND SYSTEMS FOR OPTIMIZING VIDEO STREAMING

(71) Applicant: INTUITIVE SURGICAL OPERATIONS, INC., Sunnyvale, CA (US)

(72) Inventors: Brian E. Miller, Los Gatos, CA (US); Joey Chau, Cupertino, CA (US); Govinda Payyavula, Fremont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1361 days.

(21) Appl. No.: 13/966,642

(22) Filed: Aug. 14, 2013

(65) Prior Publication Data

US 2014/0051921 A1 Feb. 20, 2014

Related U.S. Application Data

(60) Provisional application No. 61/683,493, filed on Aug. 15, 2012.

(51) Int. Cl.
*A61B 1/00* (2006.01)
*A61B 1/04* (2006.01)
(Continued)

(52) U.S. Cl.
CPC ...... *A61B 1/00009* (2013.01); *A61B 1/00011* (2013.01); *A61B 1/00045* (2013.01);
(Continued)

(58) Field of Classification Search
CPC ... A61B 1/00009; A61B 1/04; A61B 1/00045; A61B 1/00011; A61B 19/2203;
(Continued)

(56) References Cited

U.S. PATENT DOCUMENTS 5,217,453 A 6/1993 Wilk
5,659,529 A 8/1997 Maeda et al.
(Continued)

FOREIGN PATENT DOCUMENTS

JP 2002199398 A 7/2002
JP 2004120609 A 4/2004
(Continued)

OTHER PUBLICATIONS

Extended European Search Report for Application No. EP13829827, dated Jan. 25, 2016, 12 pages.
(Continued)

*Primary Examiner* — Jefferey F Harold
*Assistant Examiner* — Sean N. Haiem
(74) *Attorney, Agent, or Firm* — Jones Robb, PLLC

(57) ABSTRACT

A method for performing a surgical procedure includes adjusting an encoding configuration of a video encoder in response to receiving an input associated with a change of state of a surgical system performing the surgical procedure, and encoding image data of the surgical procedure captured after the change of state based on the adjusted encoding configuration.

20 Claims, 9 Drawing Sheets

(51) Int. Cl.
*A61B 17/00* (2006.01)
*H04N 19/172* (2014.01)
*H04N 19/114* (2014.01)
*H04N 19/137* (2014.01)
*H04N 19/164* (2014.01)
*A61B 34/30* (2016.01)
*H04N 19/146* (2014.01)
*H04N 19/166* (2014.01)
*A61B 90/00* (2016.01)

(52) U.S. Cl.
CPC .......... *A61B 1/04* (2013.01); *A61B 17/00234* (2013.01); *A61B 34/30* (2016.02); *H04N 19/114* (2014.11); *H04N 19/137* (2014.11); *H04N 19/164* (2014.11); *H04N 19/172* (2014.11); *A61B 90/361* (2016.02); *H04N 19/146* (2014.11); *H04N 19/166* (2014.11)

(58) Field of Classification Search
CPC .......... A61B 17/00234; A61B 19/5212; H04N 19/172; H04N 19/114; H04N 19/137; H04N 19/164; H04N 19/166; H04N 19/146
See application file for complete search history.

(56) References Cited

U.S. PATENT DOCUMENTS

| | | | |
|---|---|---|---|
| 6,574,207 B2 | 6/2003 | Kurtz et al. | |
| 6,587,823 B1 | 7/2003 | Kang et al. | |
| 6,873,655 B2 | 3/2005 | Comer et al. | |
| 7,984,179 B1 | 7/2011 | Huang | |
| 8,365,236 B2* | 1/2013 | Krikorian | H04L 65/4076 725/94 |
| 2002/0131391 A1 | 9/2002 | Kurtz et al. | |
| 2004/0114817 A1* | 6/2004 | Jayant | H04N 19/00 382/239 |
| 2005/0240095 A1* | 10/2005 | Schaffter | G01R 33/583 600/410 |
| 2006/0104345 A1* | 5/2006 | Millar | G08B 13/19667 375/240.01 |
| 2006/0132646 A1* | 6/2006 | Komatsu | H04N 11/20 348/441 |
| 2009/0005679 A1* | 1/2009 | Dala-Krishna | A61B 8/0883 600/437 |
| 2009/0024023 A1 | 1/2009 | Welches et al. | |
| 2009/0153472 A1 | 6/2009 | Bloem et al. | |
| 2009/0248036 A1 | 10/2009 | Hoffman et al. | |
| 2010/0157037 A1* | 6/2010 | Iketani | A61B 1/00009 348/68 |
| 2010/0182356 A1 | 7/2010 | Hoerl, Jr. et al. | |
| 2010/0283857 A1* | 11/2010 | Gopinath | G08B 13/19643 348/152 |
| 2011/0066262 A1* | 3/2011 | Kelly | G05B 23/0267 700/90 |
| 2011/0193949 A1* | 8/2011 | Nambakam | A61B 17/00 348/74 |
| 2012/0101348 A1* | 4/2012 | Yamaguchi | A61B 1/00009 600/317 |
| 2012/0109377 A1 | 5/2012 | Stern et al. | |
| 2012/0200684 A1* | 8/2012 | Glukhovsky | A61B 1/00009 348/65 |
| 2013/0300846 A1 | 11/2013 | Miller et al. | |

FOREIGN PATENT DOCUMENTS

| | | |
|---|---|---|
| JP | 2004521662 A | 7/2004 |
| JP | 2005073218 A | 3/2005 |
| JP | 2005143668 A | 6/2005 |
| JP | 2006128997 A | 5/2006 |
| JP | 2007036650 A | 2/2007 |
| JP | 2010142597 A | 7/2010 |
| WO | WO-2012033200 A1 | 3/2012 |

OTHER PUBLICATIONS

International Search Report and Written Opinion for Application No. PCT/US13/54862, dated Nov. 22, 2013, 2013, 10 pages.
Series H: Audiovisual and Multimedia Systems, Infrastructure of Audiovisual Services—Coding of Moving Video, Advanced Video Coding for Generic Audiovisual Services, Recommendation ITU-T H.264, Jun. 2011.
Arata J., et al., "A Remote Surgery Experiment between Japan-Korea using the Minimally Invasive Surgical System," Proceedings of the 2006 International Conference on Robotics and Automation, IEEE, May 2006, pp. 257-262.
Extended European Search Report for Application No. EP19202592.2 dated Feb. 17, 2020, 18 pages.
Xu J., et al., "A Content-Based Video Coding Method for Remote Monitoring of Neurosurgery," Multimedia Signal Processing, IEEE, Oct. 1, 2005, pp. 1-4.

* cited by examiner

| | A | B | C | D | E | F | G | H | I | J |
|---|---|---|---|---|---|---|---|---|---|---|
| | \multicolumn{10}{c}{P-frame / I-frame Adjustment Based on Anticipated Degree of Change at Constant Bandwidth} | | | | | | | | | |
| | Maximum BW (Mbps) | I-frame size (Kb) | P-Frame Size (Kb) | Degree of Change (1-9) | Predicted I-frames per GOP of 10 | Predicted P-frames per GOP of 10 | I-frame Rate (fps) | P-frame Rate (fps) | Frames Rate (fps) | Used BW (Mbps) |
| 1 | 1.0 | 20 | 10 | 1 | 1 | 9 | 9 | 81 | 90 | 0.99 |
| 2 | 1.0 | 20 | 10 | 3 | 3 | 7 | 21 | 49 | 70 | 0.91 |
| 3 | 1.0 | 20 | 10 | 5 | 5 | 5 | 30 | 30 | 60 | 0.90 |
| 4 | 1.0 | 20 | 10 | 7 | 7 | 3 | 35 | 15 | 50 | 0.85 |
| 5 | 1.0 | 20 | 10 | 9 | 9 | 1 | 45 | 5 | 50 | 0.95 |

FIG. 4

| | A | B | C | D | E | F | G | H | I | J |
|---|---|---|---|---|---|---|---|---|---|---|
| | \multicolumn{10}{c|}{P-frame / I-frame Adjustment Based on Anticipated Network Conditions at Minimal Field of View} |||||||||
| | Maximum BW (Mbps) | I-frame size (Kb) | P-Frame Size (Kb) | VCD Velocity (1-9) | I-frames per GOP of 10 | P-frames per GOP of 10 | I-frame Rate (fps) | P-frame Rate (fps) | Frames Rate (fps) | Used BW (Mbps) |
| 1 | 1.00 | 20 | 10 | 1 | 1 | 9 | 9 | 81 | 90 | 0.99 |
| 2 | 0.90 | 20 | 10 | 1 | 1 | 9 | 8 | 72 | 80 | 0.88 |
| 3 | 0.75 | 20 | 10 | 1 | 1 | 9 | 6 | 54 | 60 | 0.66 |
| 4 | 0.60 | 20 | 10 | 1 | 1 | 9 | 5 | 45 | 50 | 0.55 |
| 5 | 0.50 | 20 | 10 | 1 | 1 | 9 | 4 | 3 | 40 | 0.44 |

FIG. 5

METHODS AND SYSTEMS FOR OPTIMIZING VIDEO STREAMING

This application claims the benefit of U.S. Provisional Application No. 61/683,493, filed Aug. 15, 2012, which is incorporated by reference herein in its entirety.

TECHNICAL FIELD

The present disclosure is generally directed to processing video data. More particularly, aspects of the present disclosure relate to methods and systems of processing video data captured at a remote site, for example a remote surgical site during minimally invasive surgical procedures.

INTRODUCTION

Minimally invasive surgical techniques generally attempt to perform various surgical procedures while minimizing damage to healthy tissue. Minimally invasive surgical instruments (including, e.g., manual or telerobotically controlled) may be used in a variety of operations and may have various configurations. Many such instruments include, but are not limited to, a surgical end effector mounted at a distal end of a long shaft that is configured to be inserted (e.g., laparoscopically or thoracoscopically) through an opening (e.g., body wall incision, natural orifice, etc.) to reach a remote surgical site within a patient. In some instruments, an articulating wrist mechanism is mounted to the distal end of the instrument's shaft to support the end effector and alter an orientation (e.g., pitch and/or yaw) of the end effector with reference to the shaft's longitudinal axis.

The end effectors of such surgical instruments may be configured to perform various functions, including any of a variety of surgical procedures that are conventionally performed in open surgical procedures. Examples include, but are not limited to, sealing, cutting, cauterizing, ablating, suturing, stapling, etc. To control motion of an end effector, forces or torque can be transmitted from a proximal end of the surgical instrument and down the instrument shaft and to the end effector.

In telerobotic surgical systems, a surgeon manipulates various input devices at a surgeon side console (sometimes referred to herein as master inputs) to control one or more corresponding remotely-controlled surgical instruments at a remote surgical site. The inputs at the surgeon side console are communicated to a patient side cart interfaced with the remotely-controlled surgical instruments, where a corresponding teleoperated/telerobotic manipulation of the surgical instrument occurs to perform a surgical and/or other procedure on the patient at the remote surgical site.

When performing a minimally invasive surgical procedure, for example remotely via a telerobotically controlled surgical system or other minimally invasive surgical instrument (e.g., conventional manual laparoscopy or endoscopy procedures), a video display (e.g. a monitor) can be used to display images captured at the surgical site via an endoscopic camera. In robotic surgical systems, for example, the endoscopic camera may be mounted at the patient side cart and manipulated via inputs at the surgeon side console.

It may be desirable for video images captured at the surgical site to arrive at the video display with relative regularity and with minimal or no latency between the capturing of the video images and the displaying of the video images (e.g., at as high a frame rate as possible). It also may be desirable, however, to provide relatively high-fidelity video images at the video display. In this way, a video processing and display system may display high-fidelity uninterrupted "real-time" video of the surgical site, and thus provide a surgeon with a relatively clear and accurate video image of the surgical site.

If video images captured at the surgical site do not arrive at the video system with relative regularity and minimal latency, the video display might not display substantially uninterrupted real-time video of the surgical site. For example, when a data network is relied on for transferring video images captured at the surgical site to the video display, the regularity of the arrival of the video images may be affected by conditions generally associated with a data network, such as, for example, network congestion and/or network node failures. Maintaining a predetermined latency between the capturing of a video image at the surgical site and display of the video image at the video display may reduce or eliminate interruptions caused by network conditions if the predetermined latency exceeds most or all data delays (e.g., network-based delays). However, in applications where low or no latency is desired (such as in surgical applications, for example), a predetermined latency long enough to reduce or eliminate most or all interruptions may exceed a latency considered desirable for such applications.

Furthermore, if the transfer of video images between the surgical site and the display is bandwidth-limited, as is generally the case when such transfer occurs through a shared medium, such as a data network, the video images may need to be encoded/compressed to reduce the average data rate for transferring a video stream of the video images. However, known video encoding/decoding standards, such as for example, International Telecommunication Union (ITU) Telecommunication Standardization Section (ITU-T) Recommendation/Standard H.264 (also known as International Organization for Standardization/International Electrotechnical Commission (ISO/IEC), Moving Picture Expert Group version 4 (MPEG-4)) Advanced Video Coding (AVC) standard (or ISO/IEC MPEG-4 AVC standard)), which uses techniques to reduce the amount of data for transferring a video stream, may not provide sufficiently high-fidelity video images under certain circumstances. For example, for relatively large differences in consecutive video images captured (e.g., due to large motion or other changes occurring at the site), data reduction techniques used by a video encoding/decoding standard may produce a relatively low fidelity image. This can be more problematic when the differences between consecutive video images are unpredictable.

There exists a need to provide a video processing system and method that provides relatively low latency (useful for applications in which substantially real-time display is desired), as well as high fidelity of the images captured at a site and transferred for display at a video display. There also exists a need to provide a minimally invasive surgical system, such as, for example, a telerobotic surgical system that exhibits substantially uninterrupted high-fidelity video images of a surgical site with low latency at a surgeon side console display.

SUMMARY

The present disclosure solves one or more of the above-mentioned problems and/or demonstrates one or more of the above-mentioned desirable features. Other features and/or advantages may become apparent from the description that follows.

In accordance with at least one exemplary embodiment, the present disclosure contemplates a method for processing video that includes adjusting an encoding configuration of a video encoder in response to receiving an input associated with a change of state of a system performing a procedure, such as a change of state of a surgical system performing a surgical procedure. The method may further include encoding image data of the surgical procedure captured after the change of state based on the adjusted encoding configuration.

In accordance with at least another exemplary embodiment, the present disclosure contemplates a surgical system including an endoscopic image capture device and a video processor for generating video encoding configuration data to encode the image data, wherein the processor is configured to receive an input associated with a change of state of the surgical system and output adjusted video encoding configuration data based on the input.

Additional objects and advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the invention, as disclosed or claimed. The claims should be entitled to their full breadth of scope, including equivalents.

BRIEF DESCRIPTION OF THE DRAWINGS

The present disclosure can be understood from the following detailed description either alone or together with the accompanying drawings. The drawings are included to provide a further understanding of the present disclosure, and are incorporated in and constitute a part of this specification. The drawings, which are incorporated in and constitute a part of this specification, illustrate one or more embodiments of the present disclosure and, together with the description, serve to explain certain principles and operation. In the drawings.

FIG. 4 is a table used to exemplify a potential operation of a video processing technique in accordance with at least one exemplary embodiment of the present disclosure;

FIG. 5 is a table used to exemplify a potential operation of a video processing technique in accordance with another exemplary embodiment of the present disclosure;

DETAILED DESCRIPTION

Figure 1:
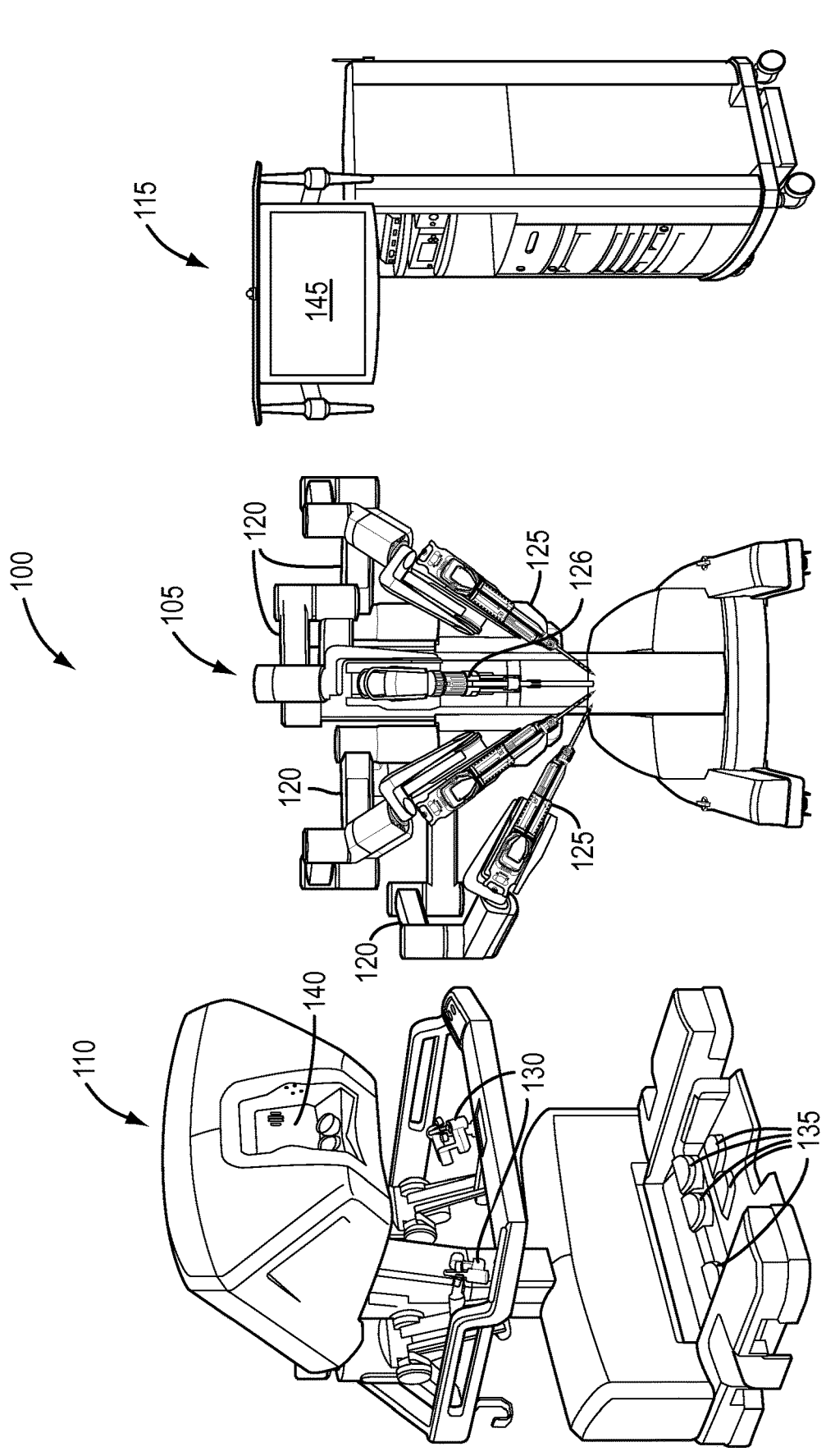
FIG. 1 is a diagrammatic view of an exemplary embodiment of a robotic surgical system in accordance with at least one exemplary embodiment of the present disclosure.

This description and the accompanying drawings illustrate exemplary embodiments and should not be taken as limiting, with the claims defining the scope of the present disclosure, including equivalents. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or the electrosurgical instrument.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In accordance with various exemplary embodiments, the present disclosure contemplates methods and systems of processing real-time video data for video applications in which the video data is captured at a site, and in particular, real-time video data for use in minimally invasive surgical systems such as, e.g., telerobotic or teleoperated surgical systems. Various exemplary embodiments, therefore, are directed to methods and systems for providing at a video display relatively uninterrupted, high-fidelity, and "real-time" video stream of video images captured at a site by, for example, an endoscopic camera. For example, various exemplary embodiments may provide a video display having a sufficiently high image frame rate to provide relatively uninterrupted video, for example, more than 15 frames per second, and a sufficiently low latency from the time the corresponding image was captured as to appear substantially instantaneous, such as, for example, less than 1.5 seconds.

In accordance with various exemplary embodiments, the various state changes that correspond to the overall use of a surgical system can be monitored and relied on as a sufficiently early indication that a likely change at a surgical site within the field of view of an image capture device, which may affect the image content data in the field of view, is anticipated. By monitoring various operational commands or other state changes occurring within the surgical system and relying on the knowledge of the functions and their likely effect on the surgical site of those operational commands/state changes, video processing methods and systems according to various exemplary embodiments can configure, in advance, an encoder to optimize the encoding of video images being captured in an active, rather than passive, manner.

Although the exemplary embodiments and description below focus mainly on generation of a real-time video stream of video images for performing minimally invasive surgical procedures, such as, for example, via robotic surgical systems, the principles of the exemplary embodiments are not so limited, and could be applied in other video processing applications, such as, for example, video generation of any video data intended to be streamed and displayed in real-time, as well as non-real-time video data (e.g., previously-recorded and stored data) intended to be streamed from a remote storage location. In various exemplary embodiments, the present disclosure may find application in various fields where video images from a remote site are captured and wherein it may be possible to know in advance that a system that may perform a function that affects the image data content in the field of view may be changing states, for example, where it may be known in advance that substances and/or other components will be leaving or entering the field of view. Thus, the effect on the image data content field of view, as a result of such a state change, can be predicted in advance so that video encoding parameters can be proactively, rather than reactively, adjusted. One nonlimiting example of a non-surgical application may include capturing images and displaying the captured images within a pipe, e.g., in the oil and/or gas industry, wherein a remotely monitored procedure is occurring and in which it can be known in advance that a certain action will be occurring that will affect the field of view, and resulting image data content, of an image capture device being used. In addition, the present disclosure may be applicable in a variety of other applications in which it may be possible to predict that network conditions of a communications network that may affect video streaming.

Furthermore, those having ordinary skill in the art will understand that the various exemplary embodiments of the present disclosure may be applied to video stream applications for streaming video images formatted for two-dimensional and three-dimensional display without departing for the scope of the present disclosure.

With reference to FIG. 1, a diagrammatic view of an exemplary embodiment of a robotic surgical system 100 is depicted. Surgical system 100 includes a patient side cart 105, a surgeon console 110, and an electronics/control console 115. It is noted that the system components in FIG. 1 are not shown in any particular positioning and can be arranged as desired, with patient side cart 105 being disposed relative to the patient so as to effect surgery on the patient. A non-limiting, exemplary embodiment of a robotic surgical system such as system 100 is a da Vinci® Si (model no. IS3000) commercialized by Intuitive Surgical, Inc. of Sunnyvale, Calif.

Robotic surgical system 100 is used to perform minimally invasive robotic surgery by interfacing with and controlling a variety of surgical instruments. The patient side cart 105 includes various arms (sometimes referred to as patient-side manipulators) 120 for holding, positioning, and manipulating the various surgical instruments and/or associated tools. As shown in FIG. 1, an arm 120 of patient side cart 105 is configured to interface with and control one or more remotely-controlled surgical instruments 125, which may include, for example, an end effector (not shown in detail). An endoscopic camera 126 also may be mounted at the patient side cart 105 to capture images at the surgical site.

Surgeon console 110 receives inputs from a surgeon by various input devices, including but not limited to, grip input levers (not shown) of one or more master grip input mechanisms 130 and foot pedals 135. The surgeon console 110 serves as a master controller by which the arms 120, surgical instruments 125, and endoscopic camera 126 at the patient side cart 105 act as a slave to implement any desired motions and accordingly perform a desired surgical procedure. However, surgical system 100 is not limited to receiving inputs at the surgeon console 110, and inputs may be received at any device which can properly realize a manipulation of the instrument(s) at the patient side cart 105. For example, an instrument at the patient side cart 105 may be manipulated at the patient side cart 105, through the surgeon console 110 in combination with other surgical instrument support device, or entirely through another surgical support device, as a result of inputs received from the user, e.g., the surgeon.

Surgeon console 110 may further include an electronic data processing system, including a processor, which may be configured to receive and process inputs from the surgeon console 110, or from any other surgical instrument support device, and control the manipulation of one or more surgical instruments at the patient side cart 105 based on such inputs. However, elements of such electronic data processing system may be provided elsewhere within surgical system 100.

An auxiliary electronics/control cart 115, which may include, for example, a processor and/or other functional units (e.g., electrosurgical energy delivery units and/or other surgical flux delivery units), receives and transmits various control signals to and from the patient side cart 105 and the surgeon console 110. Electronics/control cart 115 also can transmit light and process images (e.g., from the endoscopic camera 126 at the patient side cart 105) for display, such as, e.g., display 140 at the surgeon console 110 and/or on a display 145 associated with the electronics/control cart 115. Those having ordinary skill in the art are generally familiar with such electronics/control cart of remotely-controlled surgical systems.

In various exemplary embodiments, patient side cart 105 is positioned proximate to a patient, and the surgical instrument(s) and/or endoscopic camera remotely controlled from, for example, surgeon console 110, receives inputs from the surgeon console 110 via various master input devices, such as, for example, hand-held grip input levers of a master grip input mechanism 130, foot pedals 135, and/or camera control mechanism (not labeled). Foot pedals 135 may be used to provide command signals to deliver a flux, such as, for example, electrocautery energy, useful for performing certain procedures, such as, for example, tissue sealing and/or cutting, of a remotely-controlled surgical instrument. The hand-held grip input levers of master grip input mechanism 130 may be used to send signals to control movement of the remotely-controlled surgical instruments, including roll, translation, pitch/yaw movement, and gripping/cutting movements of some end effectors, for example.

One or more camera control mechanisms may be used to send signals to an endoscopic camera manipulator ("ECM") embedded at one of arms 120, and to an endoscopic camera, to control various aspects related to capturing and processing video images of a surgical site, such as the position/orientation of the camera with respect to the surgical site, zoom of the camera lens, focus of the camera lens, etc. By way of nonlimiting example, one or more of foot pedals 135 may be designated as a camera control mechanism. Accordingly, pressing the designated foot pedal 135 can transition the system to enter into a camera control mode in which, for example, the camera may be positioned/oriented or otherwise adjusted based on the transition, a future input ("camera-following" mode), and/or based on movement of another instrument ("instrument-following" mode). Those having ordinary skill in the art are generally familiar with the use of such teleoperated robotic surgical systems to provide input from a surgeon at a surgeon console to ultimately effect operation of both surgical instrument(s) and an endoscopic camera interfacing with a patient side cart.

Figure 2:
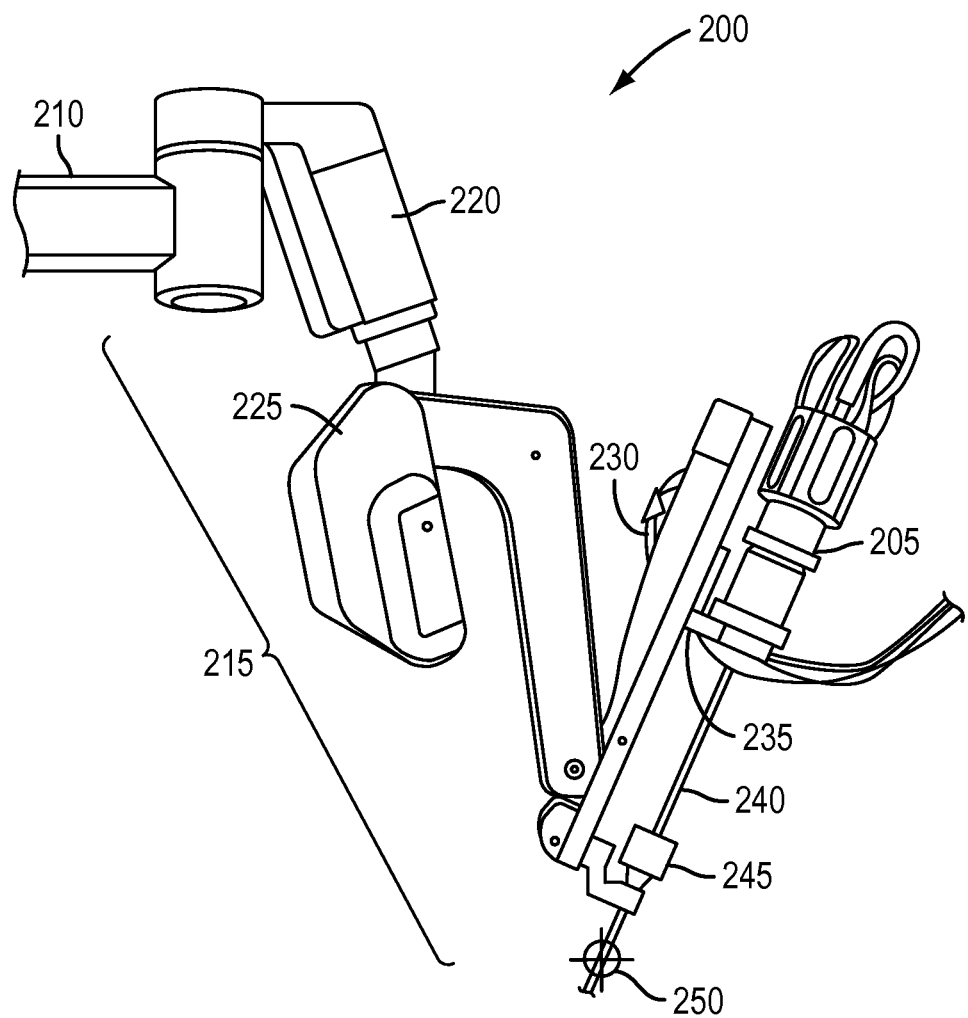
FIG. 2 is a perspective view of a portion of a camera arm of a robotic surgical system in accordance with at least one exemplary embodiment of the present disclosure.

FIG. 2 illustrates a side elevation view of a portion of a camera arm 200 with an illustrative endoscopic camera 205 mounted on the arm 200 according to an exemplary embodiment of the present teachings. In the exemplary embodiment, camera arm 200 includes a set-up portion 210 and a manipulator portion ECM 215. ECM 215 includes a yaw motion actuator 220, a pitch motion actuator 225, and an input/output motion (e.g. translation) actuator 230, all of which can be controlled by, for example, the master input grip mechanisms (e.g., master grip input mechanisms 130). Endoscopic camera 205 is mounted on carriage assembly 235, and endoscope cannula 240 is mounted on camera cannula mount 245. ECM 215 moves endoscopic camera 205 around and through remote center of motion 250. A camera arm according to an exemplary embodiment may include more or less elements than those illustrated in FIG. 2. For example, a camera arm according to the present teachings may include more, less, or none of the motion actuators set forth in FIG. 2 without departing from the spirit of the present teachings. Furthermore, the present teachings are not limited to robotic surgical systems, and thus, an endoscopic camera according to the present teachings may not be attached to a camera arm as that shown in FIG. 2, but instead may be a manually inserted and steered instrument.

In operation of a robotic surgical system as the one described with reference to FIGS. 1 and 2, a surgical procedure may include making one or more incisions in a patient's body. Such incisions are sometimes referred to as "ports", a term which may also mean a piece of equipment that is used within such an incision. In some surgical procedures, several instrument and/or camera ports may be used to provide access and imaging for a surgical site.

Figure 3:
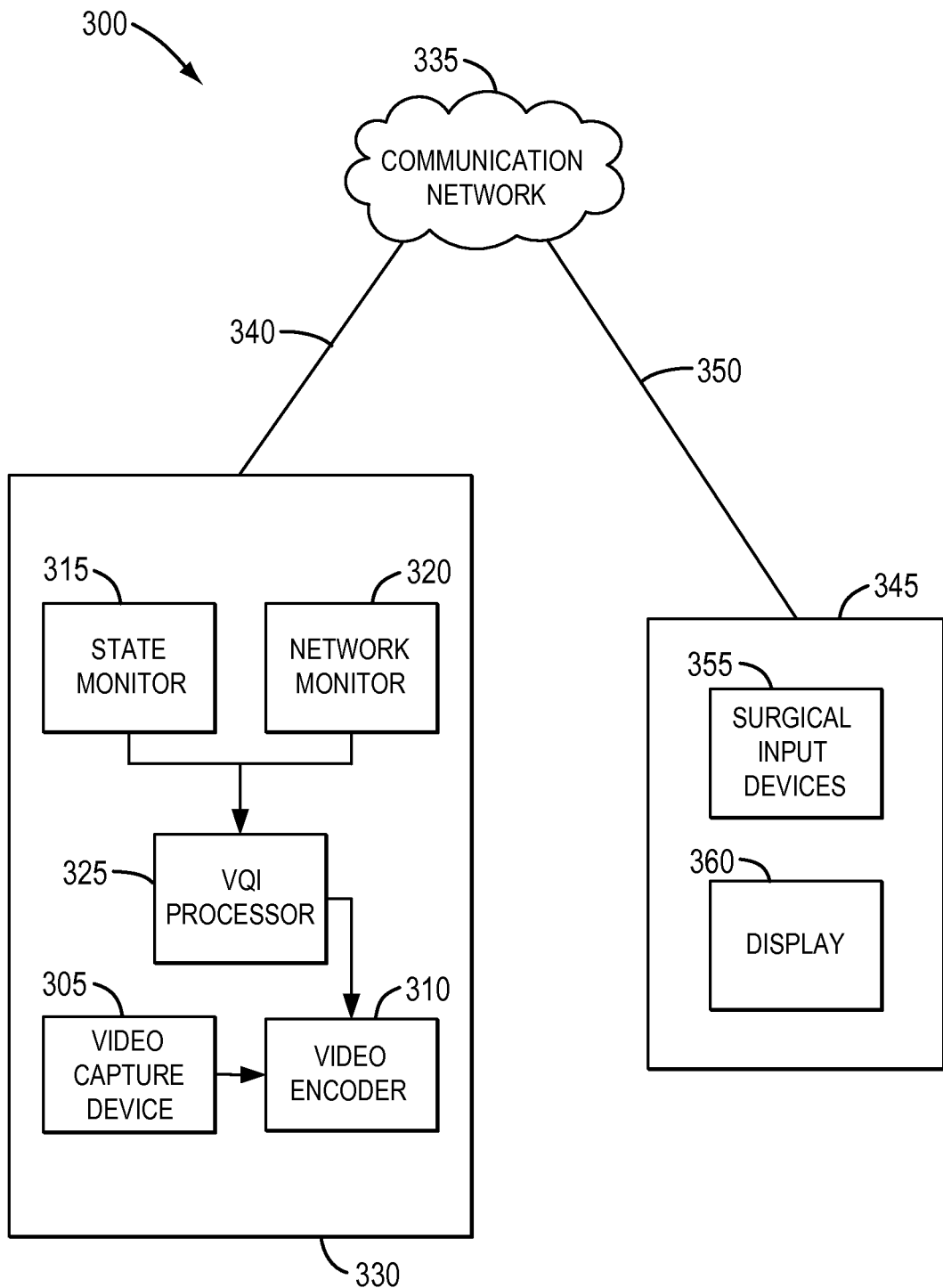
FIG. 3 is a functional block diagram of a video encoding system in accordance with at least one exemplary embodiment of the present disclosure.

FIG. 3 illustrates a functional block diagram 300 of one exemplary embodiment of a video processing system in accordance with the present disclosure. Block 305 represents a video capture device according to the present disclosure, such as, for example, endoscopic camera 205 of FIG. 2. Video capture device 305 captures image content data of a field of view of, for example, a surgical site. Block 310 represents a video encoder for encoding video images captured by video capture device 305 in one or more encoding formats, such as, for example, ITU-T Recommendation/Standard H.264 (also known as ISO/IEC MPEG-4 AVC).

Block 315 represents a state monitor for monitoring conditions that may cause a change in the image content of the field of view, and thus images captured by video capture device 305. A change in the image content of the field of view may be caused by one or more conditions, such as, for example, movement of an object within the field of view (including, for example, surgical instrument motions), movement of the video capture device, configuration of the video capture device (e.g., zooming in/out), introduction and/or removal of liquids, gases, or other substances/materials in the field of view. In various exemplary embodiments, the timing between the detection of a particular condition that may cause a change in the image content of the field of view and the corresponding change and/or the intensity of the change in the image content of the field of view that the particular condition may cause, can be anticipated and/or predicted based on the particular condition and by relying on the inputs associated with the overall control of the surgical system.

Block 320 represents a network monitor for monitoring network conditions that may affect the data rate at which encoded video frames may be transmitted to a destination through the corresponding network. Block 325 represents a so-called Video Quality Improvement (VQI) processor logically coupled to configure video encoder 310 based on conditions (e.g., changes of state and/or network conditions) that may affect the image content of the field of view of video capture device 305, and thus, the quality of the encoded video images.

According to the exemplary embodiment, VQI processor 325 receives information from state monitor 315 and/or network monitor 320 to determine an optimal configuration for video encoder 310 to encode video images (i.e., image content of the field of view) captured by video capture device 305. In particular, state monitor 315 and network monitor 320 provide information to VQI processor 325 with respect to changes that may have a future effect on the image content of the field of view captured by video capture device 305. VQI processor 325 uses this information to update configuration parameters associated with the encoding of future video images to, for example, better encode the future video images in anticipation of the changes to maintain a high fidelity, "real-time" display of the captured video images.

By way of non-limiting example, movement of an object in a remotely-controlled surgical application can include, for example, movement of one or more surgical elements at the surgical site that forms the field of view, such as, for example, activation of a surgical element to perform a particular function (e.g., activation of a cutting blade to perform a cutting procedure). Movement at the surgical site being imaged also can include, for example, movement of a body part (e.g., a beating heart, pulsing vein, etc.), introduction and/or removal of liquids and/or gases associated with, for example, blood, suction, irrigation, smoke from cauterizing tissue, introduction of fluorescent dyes or other substances to assist with imaging, etc. These movements/actions can cause a change in the image content of the field of view that, as will be explained in detailed below, may be anticipated. Thus, they can trigger VQI processor 325 to configure video encoder 310 to minimize a predicted effect of the movements/actions on the image content of the field of view.

For example, for certain remotely-controlled surgical operations, a surgeon may be required to provide one or more input commands before a particular surgical element or surgical procedure can be moved and/or operated. For a cutting procedure, for example, a first input signal generated by a command at the surgeon side console may be required to indicate a readiness to perform the procedure, which may include activation of a cutting blade at an end effector of a surgical instrument 125 embedded at a robotic arm, such as one of arms 120 of FIG. 1. The first input signal may be triggered, for example, by pressing a foot pedal, such as one of foot pedals 135 of FIG. 1. In response to the first input signal, an electronics/control cart, such as electronics/control console 115, may be configured to transition a state of the cutting element into an "armed state." Once in the "armed state," the electronics/control console may be configured to wait for a second input signal, which may be triggered, for example, by a second press of the foot pedal, before transitioning the state of the cutting element into an operational state (e.g., cause actuation of the cutting element).

In another example, an input command at the surgeon side console may be provided that places the ECM in an "in-following" state, such that the surgeon is actively controlling the arm on which the camera is mounted and thus the camera can be moved to where the surgeon controls it to move, using one of the master grip input mechanisms 135, for example. Such a command can be monitored as a state change indicative of an upcoming larger camera motion (e.g., compared to a camera not "in-following" and simply disposed in a static configuration recording images) and thus relatively dynamic and large changes in the image content of the field of view being imaged can occur in the future. Furthermore, knowledge of the particular state change, or a combination of state changes, can provide a degree of changes relative to a present image content of the field of view. Based on the information above regarding an upcoming change in the image content of the field of view, the VQI processor 325 can configure video encoder 310 to minimize a predicted effect of the upcoming change in the image content of the field of view.

The above examples are illustrative only and those having ordinary skill in the art will appreciate numerous other operational commands of the surgical system that can be monitored and known in advance to be associated with anticipated effects on the field of view being imaged, and on the image content in the field of view. The scope of the present disclosure can thus be applied to virtually any monitored state change with resulting anticipated functionality or system operation expected to result in a change of the image content in the field of view being captured.

Thus, using the preceding example as illustrative, in an exemplary embodiment of the present disclosure, block 315 can monitor the state the robotic surgical system by monitoring various inputs (e.g., one or more presses of a foot pedal 135) and provide the state of the cutting element to VQI processor 325 which, as will be explained in further detail below with respect to FIG. 4, can use this information to update configuration parameters associated with the encoding of future video images to, for example, better encode the future video images to maintain a high fidelity, "real-time" display of the captured video images in anticipation of the changes in the image content of the field of view that can be caused by operation of the cutting element.

Blocks 305, 310, 315, 320, and 325 above are illustrated in FIG. 3 as being embodied within block 330, which in an exemplary embodiment could be embodied in a patent side cart and/or an electronics/control console for performing remotely-controlled surgical procedures, such as, for example, patient side cart 105 and/or electronics/control console 115 of FIG. 1. The components depicted in FIG. 3 as embodied in block 330 are logically coupled to communication network 335 through communication link 340, and thus, at least some of the functional blocks illustrated within block 330 may be logically coupled to communication network 335, and thus may receive from, and/or provide data to, elements external to block 330 through communication network 335.

Note that although blocks 305, 310, 315, 320, and 325 above are illustrated in FIG. 3 as being embodied within block 330, exemplary embodiments of the present disclosure are not so limited, and a person having ordinary skill in the art would understand that one or more of these blocks may be embodied separately from each other and/or separately from patient side cart and/or the electronics/control console without departing from the scope of the present disclosure. A person having ordinary skill in the art also would understand that a function described as taking place within one of these functional blocks, or within one device, may be performed by multiple functional blocks and/or multiple devices in a distributed fashion without departing from the scope of the present disclosure. Furthermore, a person having ordinary skill in the art will also understand that the exemplary embodiments may include additional functional blocks, such as, for example, a communication interface for transmitting encoded video images and receiving control information, which are omitted here for simplicity.

Communication network 335 is logically coupled to functional block 345, which in an exemplary embodiment could be embodied in a surgeon console, such as, for example, surgeon console 110 of FIG. 1, through communication link 350. Surgeon console 345 is illustrated as including block 355, which represents input devices manipulatable at surgeon console 345 for performing remotely-controlled surgery. Surgeon console 345 also includes block 360, which represents a display, such as display 140 of surgeon console 110 of FIG. 1, for displaying video images of a surgical site ultimately received from the images captured by video capture device 305. Surgeon console 345 may include additional functional blocks not shown for simplicity. For example, surgeon console 345 may include a functional block for decoding encoded video images received from patient side cart 330, a functional block for storing the decoded video images, and a functional block for providing decoded images to display 360, such as those described in U.S. Provisional Application No. 61/646,597, filed May 14, 2012, and U.S. application Ser. No. 13/891,838, filed May 10, 2013, both entitled METHOD AND SYSTEM FOR VIDEO PROCESSING, which are incorporated herein by reference in their entireties. Such functional blocks have been omitted herein for simplicity.

Accordingly, data communication between patient side cart and electronics/control console 330 and surgeon console 345 including, for example, encoded images encoded by video encoder 310 and surgical control signals from surgical input devices 355, may be realized through a communication path including communication links 340 and 350 and communication network 335.

In various exemplary embodiments of the present disclosure, communication links 325 and 335 may include a wired link, a wireless link, or a combination thereof. A wired link may comprise metal, glass, air, space, or some other material as the transport media, and communication therein may be realized through a communication protocol such as, for example, Internet Protocol (IP), Ethernet, or some other communication format with which those having ordinary skill in the art are familiar, or combinations thereof. Communication network 335 may include a router, a computer system, or any other element capable of logically interconnecting multiple devices, and may be embodied as a local area network (LAN), an intranet, a wide area network (WAN), a carrier network, the internet, or some other type of communications network, or combinations thereof. Thus, patient side cart and/or electronics/control console 330 may be located either proximate or hundreds of miles from surgeon console 345, without departing from the scope of the present disclosure.

Video capture device 305 may include circuitry and/or other components for capturing video images and providing such video images to video encoder 310. Video encoder 310 may include circuitry and/or other components for encoding video images received from video capture device 305 and for transmitting encoded video images to the display 360 through communication network 320. For example, but not as limitation, video capture device 305 may include an endoscopic camera such as endoscopic camera 205 of FIG. 2. The endoscopic camera 205 can utilize a variety of imaging capture systems known to those skilled in the art, including but not limited to, for example, a digital image sensor (e.g., CCD or CMOS), a real-time magnetic resonance imaging (MRI) capture system (not shown), an ultrasound capture system (not shown), or any other type of real-time imaging capture technology that may provide real-time images to a remote location.

In various exemplary embodiments of the present disclosure, such as the exemplary embodiment illustrated in FIG. 3, video capture device 305 captures video images of a surgical site and provides the video images to video encoder 310. Video encoder 310 encodes the received video images based on a configuration set by VQI processor 325 which, as previously noted, sets such configuration based on information received from at least one of field of view state monitor 315 and network monitor 320. The encoded video images are transmitted through communication network 335 for display on display 360, which may be located at surgeon console 345, or can be separate therefrom, approximately as they were captured (e.g., in "real-time"). In such a case, it is desirable to minimize any negative effects of communication delays caused by, for example, network conditions of communication network 335, while maintaining low latency between the capturing of a video image at video capture device 305 and the display of the video image at display 360. It also is desirable to provide images with high-fidelity to those that are captured and for the images to appear at the display 360 in a relatively smooth, continuous manner with minimal jitter or other appearance of noise.

FIG. 4 is a table used to exemplify a potential operation of a VQI algorithm performed by a VQI processor, such as, for example, VQI processor 325 of FIG. 3, according to various exemplary embodiments of the present disclosure. In particular, FIG. 4 illustrates the configuration of an encoder, such as, for example, video encoder 310 of FIG. 3, based on state changes that are anticipated to affect the image content of the field of view, as monitored by, for example, state monitor 315 in FIG. 3. To illustrate principles of operation of various exemplary embodiments, FIG. 4 is based on a constant bandwidth (i.e., constant network conditions).

Column A provides an input from a network monitor, such as network monitor 320 of FIG. 3, into the VQI processor of an anticipated maximum bandwidth allocated to an exemplary embodiment of the present disclosure for transmitting encoded video images from, for example, video encoder 310 to a display 360 of FIG. 3. For purposes of the description of FIG. 4, which, as noted above, relates to the configuration of the encoder based on state changes affecting the image content of the field of view, column A remains constant along rows 1-5, (e.g., 1 megabyte per second (Mbps) in the illustrative example).

In various exemplary embodiments of the present disclosure, video images may be encoded by video encoder 310 according to the H.264 video compression standard. In H.264 encoding, as is well known to a person having ordinary skill in the art, an H.264 encoder carries out prediction, transformation, and encoding processes to produce a compressed H.264 bitstream of encoded video images. In particular, an H.264 encoder generates different types of frames, some including information necessary to reproduce the associated image (so-called intra-coded frames or i-frames), while others only include changes between a frame and one or more consecutive frames (so-called predicted frames or p-frames, or bi-predictive frames or b-frames). For simplicity, it is assumed that an H.264 encoder only generates i-frames and p-frames, but a person having ordinary skill in the art will understand that the present disclosure is not so limited and an H.264 encoder according to the present disclosure also can generate b-frames.

As those of ordinary skill in the art are also familiar with, an H.264 encoder may be configured to modify the rate at which i-frames and p-frames are generated (in frames per second (fps)), how much data is generated (bits per seconds (bps)), and the total fps (i.e., the sum of all frames generated per second). An H.264 video decoder carries out the complementary process of decoding, inverse-transforming, and reconstructing the H.264 bitstream to produce the displayed video images.

As noted above, FIG. 4 is a table for describing the operation of a VQI algorithm. Columns B and C provide exemplary sizes of i-frames and p-frames, respectively, which may be generated to encode and transmit encoded video images according to the above-referenced H.264 video compression standard. However, a person having ordinary skill in the art will recognize that various exemplary embodiments according to the present disclosure may rely on other encoding/decoding algorithms, or may rely on a different implementation of the H.264 standard (for example, the H.264 standard and the present disclosure are not limited to generating i-frames and p-frames only, and exemplary embodiments of the present disclosure may also generate b-frames).

In addition, for simplicity, in the description of FIG. 4 in general, and in columns B and C in particular, it has been assumed that all i-frames are of the same size and all p-frames are of the same size. However, a person having ordinary skill in the art will understand that the size of these frames may vary depending on, for example, characteristics of a video image captured by a corresponding video capture device, such as video capture device 305 of FIG. 3 and the amount of differences between consecutive video images. It also is assumed in Table 4 that a p-frame is half the size of an i-frame. However, a person of ordinary skill in the art will also understand that an i-frame to p-frame ratio of an encoding configuration may vary from one implementation to another, and may even vary within a single implementation, without departing from the scope of the present disclosure.

Column D provides an input from the field of view state monitor into the VQI processor of an anticipated degree of change in the image content of the field of view of a corresponding video capture device (VCD). In column D, level 1 indicates an expectation of a small change in the image content of the field of view of the VCD and level 9 indicates an expectation of a large change in the image content of the field of view of the VCD.

The anticipated degree of change in the image content of the field of view may be provided to the VQI processor by, for example, state monitor 315 of FIG. 3, and may be based on one or more inputs from a user/surgeon at a surgeon console such as, for example, input device 345 of FIG. 3. Upon receipt of an input at an input device 345 requesting an operation that can cause a change in the image content of the field of view of the VCD 305 of FIG. 3, the state monitor 315 can anticipate a degree of change that the received input may cause. The degree of change in the image content of the field of view may be based on one or multiple events that may change the image content of the field of view. Such events can include, but are not limited to, configuration of the VCD (e.g., zooming in/out and/or placing the camera "in-following"), operation of one or more surgical instruments (e.g., end effectors) within the field of view of the VCD, introduction/removal of liquids, gases, or other substances/materials to the surgical site, and movement of objects (e.g., body parts and/or surgical devices) in the field of view, without departing from the scope of the present disclosure.

In accordance with various exemplary embodiments of the present disclosure, a VQI processor may dynamically configure the encoding of captured video images based on an anticipated change in the image content of the field of view of VCD 305. Predicting a change in the image content of the field of view is made possible in various exemplary embodiments in light of the knowledge of the effect that one or more inputs within the underlying system will be anticipated of having on the image content of the field of view.

For example, within the context of robotically-controlled surgery, an input from a remote surgeon console, such as surgeon console 345 of FIG. 3, may be detected by the state monitor 315 of FIG. 3 before such input causes a change in the image content of the field of view. In particular, as explained above with respect to FIG. 3, for certain remotely-controlled surgical operations, a surgeon may be required to provide a plurality of input commands before a particular surgical element can be activated and/or moved, which allows a change in the image content of the field of view generated by movement of the particular surgical element to be anticipated. A VCD, such as endoscopic camera 126 of FIG. 1, may be configured to operate in an "in-following" mode, in which the surgeon can operate the camera to follow the motion of one of the master grip inputs, or in other exemplary embodiments to automatically "follow" movement of a particular surgical instrument, such as, for example, a cutting surgical element and/or a gripping surgical element.

When particular surgical instruments and/or the camera are actively controlled at the surgeon console and/or automatically controlled based on inputs at the surgeon console, the system is able to known in advance, as explained with respect to FIG. 3, movements and/or other functions affecting the image content of the field of view can be anticipated. In addition, knowledge about particular surgical elements and their motion and/or function and their corresponding effect on the image content of the field of view can be relied on to anticipate a variable effect of the same on the field of view. For example, a gripping motion of a jawed end effector of a surgical instrument may change the image content of the field of view less (e.g., at a slower rate) than, for example, introduction and/or removal of liquids, gases, or other substances/materials in the field of view. Similarly, such a gripping motion may have less of a change on the image content of the field of view than motion of the endoscopic camera while it is in following, for example, to move the field of view from one location in the body to another location.

Upon receiving information from the state monitor 315 regarding such change of state leading to an anticipated effect on the image content of the field of view, the VQI processor 325 may configure the video encoder 310 to produce high-fidelity encoded frames of the images of the image content of the field of view before the expected change in the image content of the field of view occurs. For example, VQI processor 325 may configure video encoder 310 to increase the i-frame rate to increase the encoding quality of captured video images. This preemptive increase in the encoding quality may obviate a decrease of quality that the anticipated change in the image content of the field of view would otherwise cause. However, as previously noted, an increase in the i-frame rate automatically increases the bit rate of transmitting encoded video images through the network. When the bandwidth allocated in various exemplary embodiments is limited, a target bit-rate must be maintained based on the available bandwidth. Thus, the total frame rate (frames/sec) of the video transmission must be decreased in order to compensate for the increased i-frame rate. Under such circumstances, according to various exemplary embodiments, the p-frame rate may be decreased to compensate for the increased i-frame rate. Note that the decrease in fps is also limited, as too low of an fps may increase latency, and thus, compromise the real-time nature of the application.

Columns E and F provide an i-frame to p-frame ratio based on an anticipated degree of change in the image content of the field of view of the VCD according to various exemplary embodiments of the present disclosure.

For simplicity, a group of pictures (GOP) of 10 has been selected to illustrate the i-frame to p-frame ratio (a GOP generally represents how many pictures/images may be provided by relying on one i-frame). However, the various exemplary embodiments of the present disclosure are not so limited and may rely on a different GOP.

As illustrated, if there is a small degree of change in the image content of the field of view of the VCD anticipated, the i-frame to p-frame ratio is at its lowest (1/9), as less i-frames may be necessary to provide a high-fidelity real-time reproduction of the captured video images. If, on the other hand, a large degree of change in the image content of the field of view of the VCD is anticipated, the i-frame to p-frame ratio is at its highest (9/1), as more i-frames may be necessary to provide a high-fidelity real-time reproduction of the captured video images.

As previously noted, however, because of the limited bandwidth available, an increase in the i-frame to p-frame ratio will require a reduction in the total number of frames that can be provided, which may increase latency and compromise the real-time nature of the application. For example, FIG. 4 illustrates that, at a relatively low i-frame to p-frame ratio, as illustrated in row 1 of the table, an i-frame rate of 9 fps and a p-frame rate of 81 fps may be realized, which produces a total of 90 fps while maintaining the used bandwidth below the maximum bandwidth of 1 Mbps (see column J, used bandwidth becomes 0.99 Mbps). On the other hand, if a significant degree of change in the image content of the field of view of the VCD is anticipated, as illustrated in row 5 of the table, an i-frame rate of 45 fps and a p-frame rate of only 5 fps may be required to maintain high fidelity. However, such configuration produces 50 fps to maintain the used bandwidth below the maximum bandwidth of 1 Mbps (see column J, used bandwidth becomes 0.95 Mbps).

The numbers/values above with respect to FIG. 4 are illustrative and non-limiting of the disclosure and those of ordinary skill in the art understand that exemplary embodiments of the present disclosure may support other number/values not illustrated herein. For example, for minimally-invasive surgical procedures a 15 fps rate may provide adequate fidelity while a 20-30 fps rate or higher may provide an optimal fidelity. For other applications, however, different fps rates than those indicated above for minimally-invasive surgical procedures may be desired without departing from the scope of the present disclosure.

Therefore, according to various exemplary embodiments of the present disclosure, conditions which may be predicted to affect the image content of the field of view of a VCD are monitored and an encoder configured to encode video images captured by the video capture device accordingly. Specifically, the encoder can be configured to encode video images captured by the VCD in anticipation of the expected change in the image content of the field of view due to a monitored and detected change of state in the overall system before the change in the image content of the field of view occurs. Thus, high-fidelity encoding may be achieved in anticipation of fidelity-lowering events before such events occur, which may obviate a low-fidelity image period generally associated with configuring a video encoder reactively (i.e., after the fidelity-lowering event occurs).

FIG. 5 is a table used to exemplify a potential operation of a VQI algorithm performed by a VQI processor, such as, for example, VQI processor 325 of FIG. 3, according to various exemplary embodiments of the present disclosure. In particular, FIG. 5 illustrates the configuration of an encoder, such as, for example, video encoder 310 of FIG. 3, based on changes in network conditions that are anticipated to affect image content captured in the field of view and transmitted to a display, as monitored by, for example, network monitor 320 in FIG. 3. FIG. 5 is based on a constant image content of the field of view (in this case, small changes in the image content of the field of view of a corresponding VCD, such as VCD 305 of FIG. 3), according to various exemplary embodiments of the present disclosure.

Column A provides an input from the network monitor into the VQI processor of an anticipated maximum bandwidth allocated to an exemplary embodiment of the present disclosure for transmitting encoded video images, for example, from video encoder 310 to display 360 of FIG. 3. However, in contrast to the exemplary conditions set forth in FIG. 4, in which column A remained constant, FIG. 5 illustrates the operation of a VQI algorithm under varying network conditions resulting in variable bandwidth across the communication network 335.

As in FIG. 4, columns B and C provide exemplary sizes of i-frames and p-frames, respectively, which may be generated to encode and transmit encoded video images according, for example, to an H.264 video compression standard. Accordingly, these columns are not described here.

With respect to column D, as in FIG. 4, it provides an input from the field of view state monitor of an anticipated degree of change in the image content of the field of view of a corresponding VCD. However, as noted above, FIG. 5 illustrates an exemplary operation of a VQI algorithm under varying network conditions. Accordingly, to particularly illustrate the effect of varying network conditions independently from other state changes, in FIG. 5, column D remains constant through rows 1-5.

Those having ordinary skill in the art would understand that FIG. 5 illustrates unvarying state conditions coming from the state monitor 315, with VCD degree of change being an exemplary monitored state condition for simplification to provide an understanding of how various exemplary embodiments implement a VQI algorithm to accommodate variations in network conditions, as monitored by network monitor 320, for example.

Columns E and F provide an i-frame to p-frame ratio based on an anticipated degree of change in the image content of the field of view of a VCD. Because, as noted above, FIG. 5 is directed to the operation of a VQI algorithm under varying network conditions instead of state changes affecting the image content of the field of view of the VCD (e.g., such as operating of surgical elements), column D is remains constant along rows 1-5. Accordingly, since columns E and F depend on the values set forth in column D, columns E and F also remain constant through rows 1-5.

Columns G, H, and I of FIG. 5 illustrate a configuration of an encoder according to various exemplary embodiments of the present disclosure. As the anticipated maximum bandwidth of the network decreases, an exemplary embodiment of a VQI processor according to the present disclosure adjusts the i-frame and p-frame rates, as shown in columns G and H, to maintain a desired i-frame to p-frame ratio. As a result, the total frame rate decreases, as shown in column I. For example, FIG. 5 illustrates that, when the anticipated maximum rate is 1 Mbps, as illustrated in row 1 of the table, an i-frame rate of 9 frames per second (fps) and a p-frame rate of 81 fps may be realized, which produces a total of 90 fps while maintaining the used bandwidth below the maximum bandwidth of 1 Mbps (see column J, used bandwidth becomes 0.099 Mbps). As the anticipated maximum bandwidth decreases, as illustrated in, for example, row 5 of the table, both the i-frame rate and the p-frame rate are reduced, and thus, the total fps is reduced to 40 fps to maintain the used bandwidth below the maximum bandwidth of 0.5 Mbps (see column J, used bandwidth becomes 0.44 Mbps).

Therefore, according to various exemplary embodiments of the present disclosure, one or more conditions that may be predicted to affect the maximum bandwidth available to transmit encoded video images are monitored and an encoder configured to encode video images captured by the video capture device based on the conditions. Specifically, the encoder may be configured to encode video images captured by the video capture device in anticipation of the expected change in the maximum bandwidth available and before the change in the maximum bandwidth available occurs. Thus, high-fidelity, "real-time" encoding may be achieved in anticipation of fidelity-lowering network condition events before such events occur, which may obviate a low-fidelity image period generally associated with configuring a video encoder reactively (i.e., after the fidelity-lowering event occurs).

The numbers/values set forth in FIG. 4 and FIG. 5, and used in their respective descriptions, are prophetic examples that have been chosen only to aid in an understanding of certain principles of operation of exemplary embodiments of the present disclosure. Those of ordinary skill in the art understand that these numbers/values are not limiting and exemplary embodiments of the present disclosure may support other number/values not illustrated herein.

Although FIG. 4 illustrates a VQI algorithm according to various embodiments of the present disclosure in view of anticipated changes to an image content of the field of view of a VCD, and FIG. 5 illustrates the VQI algorithm according to various embodiments of the present disclosure in view of anticipated changes to the anticipated bandwidth available for transmitting encoded video images, the present disclosure is not so limited. A person having ordinary skill in the art will understand that the VQI algorithm may configure the encoding of video images based on a combination of both changes of state predicted to affect the image content of the field of view and corresponding captured images, as well as network conditions (e.g., bandwidth) changes without departing from the scope of the present disclosure.

Figure 6:
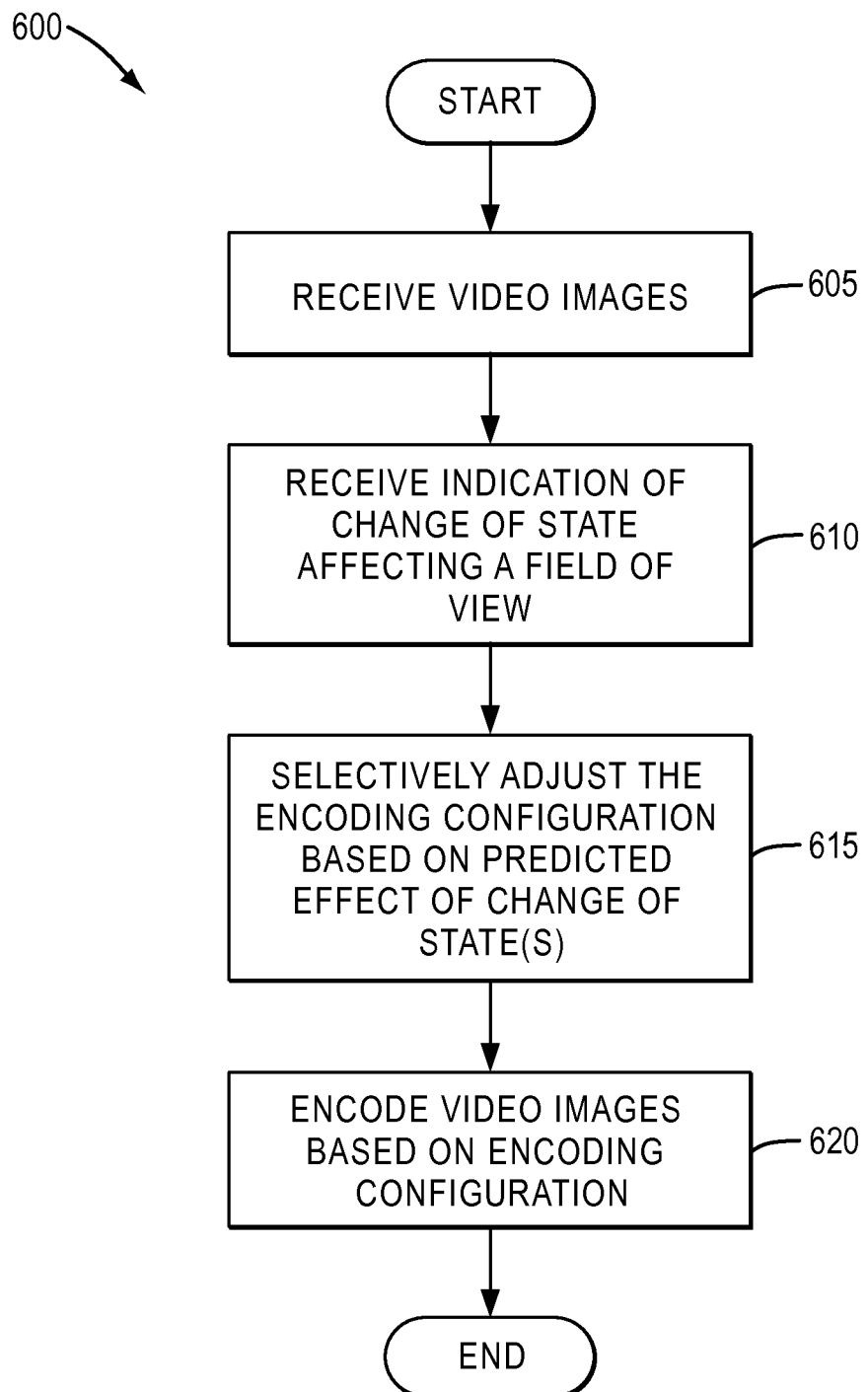
FIG. 6 is a flow diagram depicting a method for processing video in accordance with at least one exemplary embodiment of the present disclosure.

FIG. 6 is a flow diagram depicting a method for processing video in accordance with at least one exemplary embodiment of the present disclosure. At step 605, the method includes receiving video images of, for example, a surgical site, captured by a video capture device such as, for example, video capture device 305 of FIG. 3. At step 610, the method includes receiving an indication of a change of state that can affect an image content of the field of view of the video capture device. As explained in detail with respect to FIG. 3 and FIG. 4 above, a change of state that can affect the image content of the field of view may be triggered by one or more system conditions, such as, for example, a movement of a surgical element, movement of the video capture device, configuration of the video capture device (e.g., zooming in/out), and/or application/removal of liquids, gases, or other substances/materials at the surgical site, and the degree of change in the image content of the field of view may be anticipated based on the particular condition. Further, as explained above, the system conditions can be altered by various input commands received at the surgeon side console and/or automatic functions occurring following an input command or change in operational state provided at the surgeon console.

At step 615, the method includes selectively adjusting an encoding configuration for encoding captured video images based on a predicted effect of the change of state in the image content of the field of view indicated by the received indication at step 610. The change in the encoding configuration may include adjusting the resolution of at least one of the future images to be encoded, or adjusting the image frame generation/transmission rate for generating/transmitting encoded video images to receiving system such as, for example, display 360 of FIG. 3. At step 620, the method includes encoding captured video images based on the adjusted encoding configuration.

Figure 7:
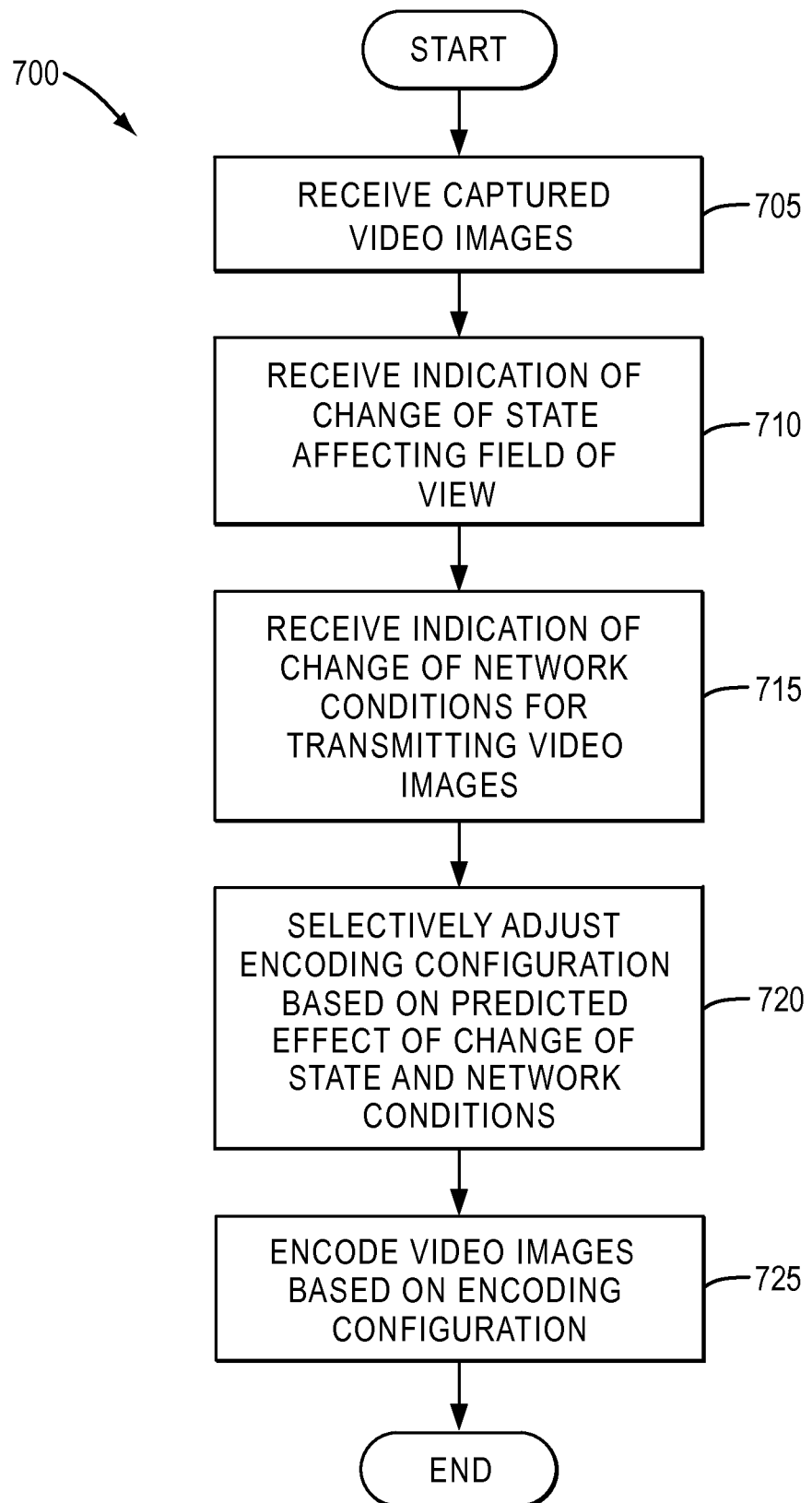
FIG. 7 is a flow diagram depicting a method for processing video in accordance with another exemplary embodiment of the present disclosure.

Thus, in accordance with various exemplary embodiments of the present disclosure, a video image encoder may be configured, via VQI, for example, to encode video images based on an anticipated effect of a monitored condition on a field of view of a video capture device. Thus, high-fidelity encoding may be achieved in anticipation of fidelity-lowering events before such events occur, which may obviate a low-fidelity image period generally associated with configuring a video encoder reactively (i.e., after and in response to the fidelity-lowering event occurs). FIG. 7 is a flow diagram depicting a method for processing video in accordance with another exemplary embodiment of the present disclosure. At step 705, the method includes receiving video images captured at, for example, a surgical site, by a video capture device such as, for example, video capture device 305 of FIG. 3. At step 710, the method includes receiving an indication of a change of state that can affect an image content of the field of view of the video capture device. As noted above with respect to FIG. 6 (and further with respect to FIG. 3 and FIG. 4), a change of state that can affect the image content of the field of view may be caused by one or more system conditions, such as, for example, a movement of a surgical element, movement of the video capture device (e.g., endoscopic camera 205), configuration of the video capture device (e.g., zooming in/out), and/or application/removal of liquids, gases, or other substances/materials at the surgical site, and the degree of change in the image content of the field of view may be anticipated based on the particular condition.

At step 715, the method includes receiving an indication of a change of network conditions that can affect transmission of encoded video images to a receiving system such as, for example, display 360 of FIG. 3. A change of network conditions may be caused by, for example, congestion of a network such as, for example, communication network 335 of FIG. 3, used to transfer encoded video images to a receiving system. Network conditions may be determined by, for example, a determination of loss packets or a measure of packet data latency through the network.

At step 720, the method includes selectively adjusting an encoding configuration for encoding captured video images based on a predicted effect of the change in the image content of the field of view indicated by the received indication and the anticipated effect of the network conditions in the transmission of encoded video images to their destination. The change in the encoding configuration may include adjusting the resolution of at least one of the future images to be encoded, or adjusting the image frame generation/transmission rate for generating/transmitting encoded video images to receiving system such as, for example, display 360 of FIG. 3. At step 725, the method includes encoding captured video images based on the adjusted encoding configuration.

Thus, in accordance with various exemplary embodiments of the present disclosure, a video image encoder may be configured, via a VQI, for example, to encode video images based on an anticipated effect of a monitored state condition on an image content of the field of view of a video capture device and/or conditions of a network used to transmit encoded video images to a destination. Various exemplary embodiments, therefore, further permit monitoring state and/or network conditions of the robotic surgical system to not only predict the occurrence of conditions anticipated to affect the image content of the field of view, but also the nature (e.g., degree) of the anticipated effect on the image content of the field of view (for example, anticipating movement of a jawed end effector in comparison to large fluid motion caused by suction, irrigation, and/or a cautery procedure; or movement of a jawed end effector in comparison to movement of the endoscopic camera from one location to another while it is "in following.")

Figure 8:
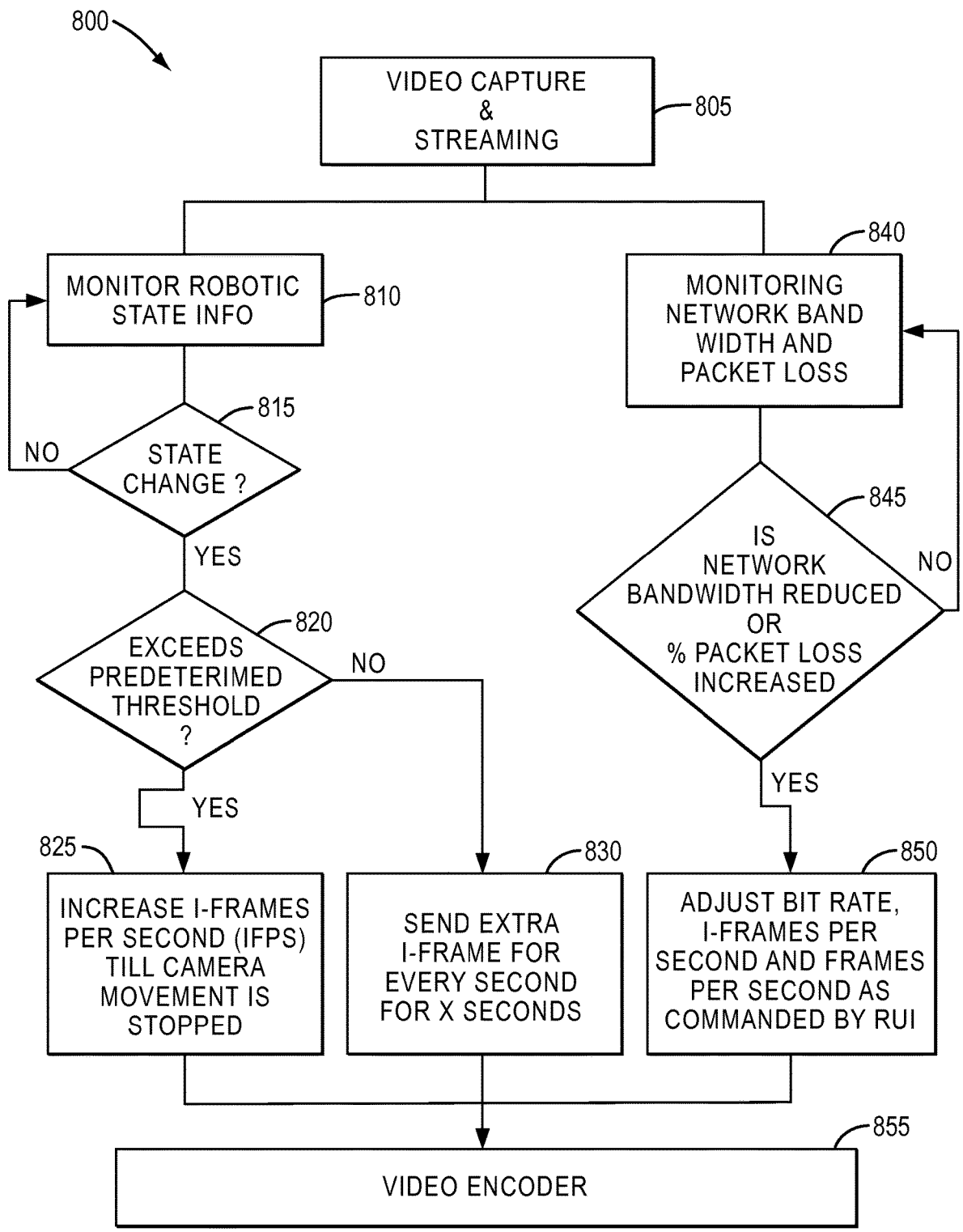
FIG. 8 is a flow diagram depicting a method for processing video in accordance with yet another exemplary embodiment of the present disclosure.

FIG. 8 is a flow diagram depicting a method for processing video in accordance with yet another exemplary embodiment of the present disclosure. At step 805 a video capture, such as, for example, an endoscopic camera or other video capture device mounted at patient side cart 330 of FIG. 3, starts capturing video images of a remote surgical site, and based on a predetermined encoding configuration, streams the captured video images to a remote display, such as to a display 360 of surgeon console 345 of FIG. 3. The transmission of the video images from the camera at the remote surgical site to the display occurs through a communication network such as communication network 335 of FIG. 3.

At step 810, the method includes monitoring conditions at the video capture and encoding system elements of the underlying system that may affect an image content of the field of view, and thus captured images, of the video capture device of the video capture and encoding system. As explained in detail with respect to FIG. 3 and FIG. 4, in remotely-controlled surgical systems, for example, movement of a robotic arm and/or a surgical instrument within the field of view, camera zoom/speed, or application/removal of substances such as liquids or gases to a surgical site within the field of view may affect the image content of the field of view of a video capture device capturing video of the surgical site for performing remotely-controlled surgery, and the degree of change in the image content of the field of view may be anticipated based on the particular condition.

At step 815, the method includes determining if a change of state predicted to affect the image content of the field of view has occurred. If a change of state has occurred, at step 820 the method includes determining if the anticipated effect of the change of state in the image content of the field of view is expected to exceed a predetermined threshold. The predetermined threshold depends on the particular change of state and could be based, for example, on movement of the image capture device capturing the image content of the field of view, an adjustment (e.g., zoom in/out) of the field of view, a movement of an instrument within the field of view, or any other action which may be expected to cause a change in the image content of the field of view.

For example, in various exemplary embodiments of the present disclosure, an input such as activating (e.g., depressing) a foot pedal, for example, may indicate a transition into a camera control mode, and a further input for adjusting the position/orientation of the camera may be predicted to cause a particular change in the current field of view. The predicted change may be based on the expected velocity of the camera based on the input and/or current conditions at the field of view (e.g., other movement being experienced or expected to be experienced within the field of view). Accordingly, a measurable value, such as the velocity of the adjustment of the camera, may be compared to a predetermined camera velocity threshold to determine the need and degree for an adjustment of encoding parameters.

It is noted that the determination of an expected degree of change in the image content of the field of view, and an associated change in the encoding parameters, may occur at the remote site (based on inputs from the user) or at the surgeon console (provided to the remote site from the surgeon console) without departing from the scope of the present disclosure. For example, in various exemplary embodiments, upon receiving an input for adjusting the position/orientation of the camera at the surgeon console, a processing unit at the surgeon console may predict a change in the current field of view, and image content therein, based on the expected velocity of the camera caused by the input and may determine the need and degree for an adjustment of the encoding parameters. The processing unit may further determine the corresponding adjustment of the encoding parameters and provide the encoding parameters to the patient side cart for configuration of the CODEC.

If the anticipated effect of the change of state exceeds a predetermined threshold, then, at step 825, encoding configuration parameters are adjusted to minimize the anticipated effect. The adjustment may include, for example, increasing the i-frame rate according to a predetermined profile, proportionally to the anticipated effect, or based on a function according to the anticipated effect, without departing from the scope of the present disclosure. For example, and not as limitation, when using the velocity of the image capture device as the measure of the change of state, a change in encoding configuration parameters, such as i-frame rate, may be proportional to the velocity of the image capture device in excess to the predetermined threshold.

If the anticipated effect of the change of state does not exceed the predetermined threshold, then, at step 830, encoding configuration parameters may be left unchanged or in a predetermined default configuration state. If other conditions, such as available bandwidth, are favorable, the change of state may nevertheless cause configuration parameters to be adjusted to, for example, minimize any effect of the change of state. This adjustment may include, for example, increasing the i-frame rate by a predetermined amount (e.g., one additional i-frame per second) for a predetermined amount of time (e.g., 5 seconds), or may include an update of the predetermined default configuration state.

At step 840, the method also can include monitoring network conditions of a network between the video capture device and the remote display. Network conditions that may be monitored include, for example, available bandwidth for transmitting encoded video images and/or a packet loss rate. At step 845, the method includes determining if a change in network conditions has occurred, such as a reduction in available bandwidth, or an increase in the percentage of packets lost. At step 850, if the network conditions have changed (e.g., decrease in available bandwidth), encoding configuration parameters are adjusted to overcome the effects of the change in network conditions by, for example, decreasing the transmission data rate (i.e., bit rate), decreasing the i-frame rate, and/or decreasing the overall frame rate of frames transmitted to the receiving system. At step 855, the method includes providing any adjusted encoding configuration parameters to a video encoder such as, for example, video encoder 310 of FIG. 3.

Thus, in accordance with various exemplary embodiments of the present disclosure, a video image encoder may be configured to encode video images based on an anticipated effect of a monitored condition on a field of view of a video capture device and conditions of a network used to transmit encoded video images to a destination. Thus, high-fidelity encoding may be achieved in anticipation of fidelity-lowering events before such events occur, which may obviate a low-fidelity image period generally associated with configuring a video encoder reactively (i.e., after the fidelity-lowering event occurs).

Figure 9:
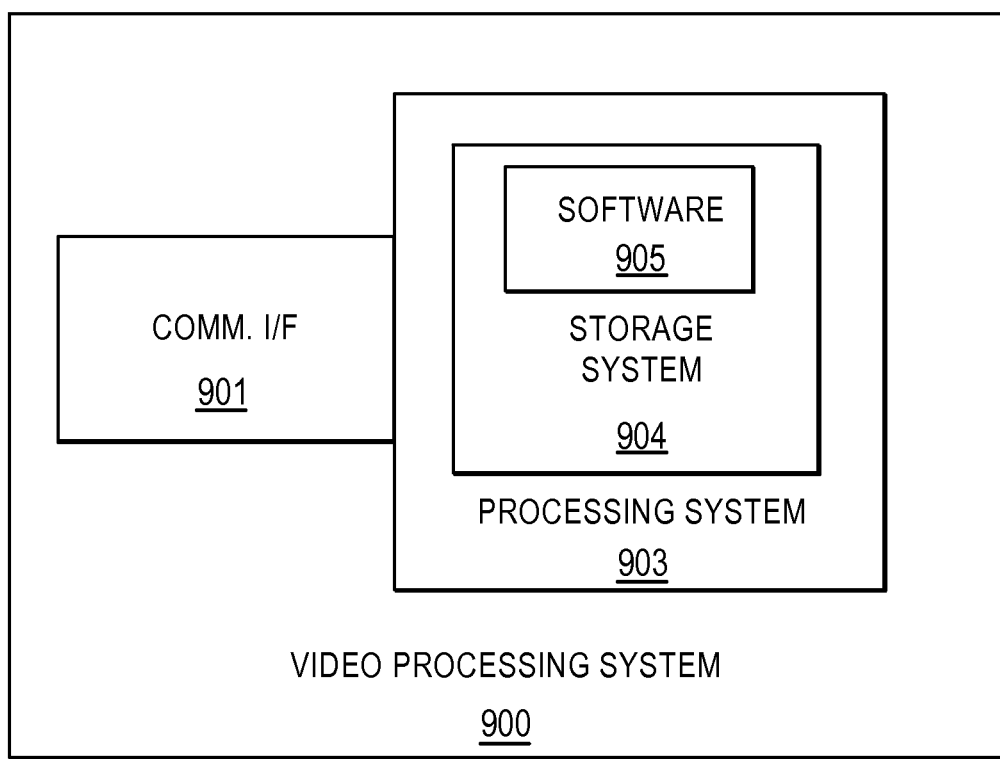
FIG. 9 schematically illustrates a video processing system according to at least one exemplary embodiment of the present disclosure.

FIG. 9 illustrates an exemplary embodiment of a video processing system according to the present disclosure. Video processing system 900 is an example of VQI processor 325, although a person of ordinary skill in the art would recognize that a VQI processor according to the present disclosure may be configured differently. Video processor 900 comprises communication interface 901 and processing system 903. Processing system 903 is linked to communication interface 901. Processing system 903 includes processing circuitry and storage system 904 that stores software 905. Video processor 900 may include other well-known components such as a power system, a battery, and/or an enclosure that are not shown for clarity.

Communication interface 901 comprises at least communication circuitry to interface with devices external to video processing system 900, and may include circuitry for wired and/or wireless communication. Furthermore, communication interface 901 may be configured to communicate with other systems and/or elements for implementing at least some of the features performed by various exemplary embodiments of the present disclosure, such as state monitor 315 of FIG. 3, network monitor 320 of FIG. 3, and video encoder 310 of FIG. 3, described above. Communication interface 901 may also include a memory device, software, processing circuitry, or some other communication device, or realize the types of communication referenced in the present disclosure.

Processing system 903 may comprise a microprocessor and other circuitry that retrieves and executes software 905 from storage system 904. Storage system 904 comprises a disk drive, flash drive, data storage circuitry, or some other memory apparatus. Processing system 903 is typically mounted on a circuit board that may also hold storage system 904 and/or portions of communication interface 901.

Software 905 comprises computer programs, firmware, or some other form of machine-readable processing instructions to implement, for example, algorithms such as the VQI algorithm described in the present disclosure. Software 905 may include an operating system, utilities, drivers, network interfaces, applications, or some other type of software. When executed by processing system 903, software 905 directs processing system 903 to operate video processor 900 as described herein for VQI processor 325.

The various exemplary embodiments of the present disclosure can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to effect the various responses and signal processing in accordance with the various exemplary embodiments of the present disclosure can be implemented by a processor of or in conjunction with the electronics/control console 115, such as an electrosurgical processing unit discussed above, and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

As described above, the methods and systems in accordance with various exemplary embodiments can be used in conjunction with a surgical instrument having an end effector configured to perform multiple surgical procedures via components that are actuated via a transmission mechanism at the proximal end of the instrument. Further, according to an aspect of the embodiments, any combinations of the described features, functions and/or operations can be provided.

The methods and systems in accordance with various exemplary embodiments have been explain within the context of encoding/decoding and transmission of images according to the H.264 encoding/decoding protocol. However, a person having ordinary skill in the art understands that the present disclosure is not so limited, and some or all elements of the present disclosure can be used within the context of one or more other encoding/decoding protocols without departing from the scope of the present disclosure.

Other embodiments of the invention will be apparent to those skilled in the art from consideration of the specification and practice of the present disclosure and claims herein. It is intended that the specification and examples be considered as exemplary only, with a scope being indicated by the claims, including equivalents.

What is claimed is:

1. A method of processing video of a surgical procedure captured by an image capturing device of a surgical system, the method comprising:
adjusting an encoding configuration of a video encoder in response to an input that effects a change of state of the surgical system performing the surgical procedure, wherein:
the input comprises a control command input at an input device of the surgical system, the input device being operably coupled to control at least one of the image capturing device and a surgical instrument of the surgical system, and
the input and adjusting occur in advance of the change of state of the surgical system; and
encoding image data of the surgical procedure captured after the change of state, the encoding using the video encoder having the adjusted encoding configuration.

2. The method of claim 1, wherein:
adjusting the encoding configuration comprises increasing an image encoding resolution for encoding at least one image frame of the image data.

3. The method of claim 2, wherein:
adjusting the encoding configuration further comprises decreasing an image encoding rate for encoding the image data.

4. The method of claim 1, wherein:
encoding the image data based on the adjusted encoding configuration comprises generating intra-frames (i-frames) at an i-frame rate and generating predictive inter-frames (p-frames) at a p-frame rate; and
adjusting the encoding configuration comprises adjusting the i-frame rate.

5. The method of claim 4, wherein:
adjusting the encoding configuration further comprises adjusting the p-frame rate.

6. The method of claim 5, further comprising:
transmitting the generated i-frames and p-frames to a video decoder at a predetermined transmission data rate wherein:
the adjusting of the p-frame rate is based on the adjusting of the i-frame rate and the predetermined transmission data rate.

7. The method of claim 1, wherein:
the input that effects the change of state comprises at least one of an input that effects movement of the image capture device, an input that effects an adjustment of a field of view of the image capture device, and an input that effects movement of an element within the field of view of the image capture device; and
adjusting the encoding configuration is based on a predicted difference between current captured image data and anticipated captured image data as affected by the change of state.

8. The method of claim 1, further comprising:
adjusting the encoding configuration in response to receiving a link status input indicative of a change of a bandwidth available for transmission of encoded images.

9. A surgical system comprising:
an endoscopic image capture device for capturing image data of a surgical site during a surgical procedure;
an input device for receiving a control command input that effects a change of state of the surgical system, the input device being operably coupled to control at least one of the endoscopic image capture device and a surgical instrument of the surgical system; and
a video processor for generating video encoding configuration data to encode the image data, the video processor configured to:
output adjusted video encoding configuration data based on the received input, wherein the input and the output occur before the change of state.

10. The surgical system of claim 9, further comprising:
an image encoder logically coupled to the video processor and the endoscopic image capture device, the image encoder configured to:
receive from the video processor the video encoding configuration data;
receive from the endoscopic image capture device the image data; and encode the received image data based on the received video encoding configuration data.

11. The surgical system of claim 10, further comprising:
an output communication interface logically coupled to the image encoder to provide to a display the encoded image data.

12. The surgical system of claim 10, wherein:
the adjusted video encoding configuration data comprises an intra-frames (i-frames) rate parameter and a predictive inter-frames (p-frames) rate parameter for encoding the image data based on an anticipated effect of the change of state.

13. The surgical system of claim 12, further comprising:
an output communication interface logically coupled to the image encoder to provide to a display through a communication link the encoded image data, wherein:
the video processor is further configured to receive a link status input indicative of a communication link condition; and
the adjusted video encoding configuration data comprising the intra-frames (i-frames) rate parameter and the predictive inter-frames (p-frames) rate parameter for encoding the captured image data being further based on the link status input indicative of the communication link condition.

14. The surgical system of claim 9, wherein:
the adjusted video encoding configuration data comprises an image encoding resolution for encoding the image data based on an anticipated effect of the change of state on the image data.

15. The surgical system of claim 14, wherein:
the adjusted video encoding configuration data further comprises an image encoding rate for encoding the image data based on the anticipated effect of the change of state on the image data.

16. The surgical system of claim 9, wherein:
the adjusted video encoding configuration data further comprises an image encoding rate for encoding the image data based on an anticipated effect of the change of state on the image data.

17. The surgical system of claim 9, further comprising:
an output communication interface logically coupled to an image encoder to provide to a display encoded image data through a communication link, wherein:
the video processor is further configured to receive a link status input indicative of a condition of the communication link; and
the adjusted video encoding configuration data further comprises an image encoding resolution for encoding the image data based on the link status input indicative of the communication link condition.

18. The surgical system of claim 17, wherein:
the adjusted video encoding configuration data further comprises an image encoding rate for encoding the image data based on the link status input indicative of the communication link condition.

19. The surgical system of claim 9, wherein the input that effects a change of state of the surgical system comprises at least one of an input that effects movement of the image capture device, an input that effects an adjustment of a field of view of the image capture device, and an input that effects movement of an element within the field of view of the image capture device.

20. A method of processing video of a surgical procedure captured by an image capturing device of a surgical system, the method comprising:
adjusting an encoding configuration of a video encoder in response to an input that effects a change of state of the surgical system performing the surgical procedure, wherein:
the input comprises a control command input at an input device of the surgical system, the input comprising at least one of an input that effects movement of the image capture device, an input that effects an adjustment of a field of view of the image capture device, and an input that effects movement of an element within the field of view of the image capture device,
the input device being operably coupled to control at least one of the image capturing device and a surgical instrument of the surgical system, and
the input and adjusting occur in advance of the change of state of the surgical system; and
encoding image data of the surgical procedure captured after the change of state, the encoding using the video encoder having the adjusted encoding configuration.

* * * * *